US00PP30245P2

(12) United States Plant Patent
Moucheboeuf

(10) Patent No.: US PP30,245 P2
(45) Date of Patent: Feb. 26, 2019

(54) ***DIANTHUS* PLANT NAMED 'WP17 PIE54'**

(50) Latin Name: ***Dianthus* x *allwoodii* hort.**
Varietal Denomination: WP17 PIE54

(71) Applicant: Plant Genetics International Ltd., Hambrook, West Sussex (GB)

(72) Inventor: Laetitia Moucheboeuf, Devon (GB)

(73) Assignee: Plant Genetics International, LTD., Hambrook (GB)

( * ) Notice: Subject to any disclaimer, the term of this patent is extended or adjusted under 35 U.S.C. 154(b) by 0 days.

(21) Appl. No.: 15/731,701

(22) Filed: Jul. 19, 2017

(51) Int. Cl.
*A01H 5/02* (2018.01)
*A01H 6/30* (2018.01)

(52) U.S. Cl.
USPC ..... Plt./277
CPC ..... *A01H 6/305* (2018.05)

(58) Field of Classification Search
USPC ..... Plt./273, 277, 276, 278
CPC ..... A01H 5/02; A01H 5/0233; A01H 6/305; A01H 5/00
See application file for complete search history.

(56) References Cited

PUBLICATIONS

Germania Seed Company Green Leaf—Perennial Starter Plants 2017, retrieved on Jun. 26, 2018, retrieved from the Internet at https://www.germaniaseed.com/pdf/2018/701_greenleaf.pdf, pp. 1, 4, 17. (Year: 2017).*

Plant Haven American Pie *Dianthus* Bumbleberry Pie, retrieved on Jun. 26, 2018, retrieved from the Internet at http://planthaven.com/wp-content/uploads/2016/07/Dianthus-AMERICAN-PIE%E2%84%A2-Bumbleberry-Pie-PK.pdf, one page. (Year: 2018).*

* cited by examiner

*Primary Examiner* — June Hwu
(74) *Attorney, Agent, or Firm* — Bethany R. Roahrig; Cochran Freund & Young LLC

(57) ABSTRACT

A new cultivar of *Dianthus* plant named 'WP17 PIE54' that is characterized by a compact mounding habit, large single magenta flowers with a darker contrasting band color, blooming from May through October, with a strong, pleasant spicy fragrance, strongly glaucous blue green foliage and is suitable for use as a flowering plant in pots and containers as well as for use as a cut flower and in bouquets, is disclosed.

2 Drawing Sheets

Genus and species: *Dianthus* x *allwoodii* hort.
Variety denomination: 'WP17 PIE54'.

BACKGROUND OF THE NEW PLANT

The present invention relates to a new and distinct cultivar of hardy *Dianthus*, commonly known as Garden Pink, which is grown for use as a flowering plant for pots and containers and for planting in the garden and landscape. The new cultivar is known botanically as *Dianthus* x *allwoodii* hort. and will be referred to hereinafter by the cultivar name 'WP17 PIE54'.

'WP17 PIE54' is a complex hybrid plant that is the product of a long-term breeding program conducted in a cultivated area of Houndspool, Dawlish, Devon, United Kingdom. 'WP17 PIE54' was selected in 2009 for its large single vibrant magenta flowers, its strong, pleasant spicy fragrance, and glaucous blue-green foliage.

'WP17 PIE54' arose and was selected as a seedling which resulted from the controlled pollination of two of the inventor's prior selections of *Dianthus*. The male parent is *Dianthus* code name 'GI52' (unpatented and unreleased) and the female parent is *Dianthus* code name 'Tricia' (unpatented and unreleased). The male parent and female parent had both been grown within the inventor's stock of breeding lines.

Asexual reproduction of 'WP17 PIE54' was first accomplished in 2009 in a cultivated area of Houndspool, United Kingdom using the propagation method of shoot cuttings.

'WP17 PIE54' has been determined to be stable and reproduces true to type in successive generations of asexual propagation.

SUMMARY

The following traits have been repeatedly observed and represent the characteristics of the new *Dianthus* cultivar 'WP17 PIE54'. 'WP17 PIE54' has not been tested under all possible conditions and phenotypic differences may be observed with variations in environmental, climatic and cultural conditions, however, without any variance in genotype.

1. 'WP17 PIE54' exhibits a compact mounding habit.
2. 'WP17 PIE54' bears large single magenta flowers with a darker magenta band.
3. The petals of 'WP17 PIE54' are flat.
4. 'WP17 PIE54' blooms from May through October.
5. The flowers of 'WP17 PIE54' exhibit a strong, pleasant spicy fragrance.
6. 'WP17 PIE54' exhibits strongly glaucous blue-green foliage.
7. At maturity, the height of the foliage mound of 'WP17 PIE54' is 45 cm, and the width is 30 cm to 35 cm.
8. 'WP17 PIE54' is perennial and is hardy at least to minus 15° Centigrade.
9. 'WP17 PIE54' is suitable for use as a flowering plant in pots and containers, and for use as a cut flower and in bouquets.

BRIEF DESCRIPTION OF THE PHOTOGRAPHS

The accompanying color photographs illustrate the overall appearance of the new *Dianthus* variety 'WP17 PIE54' showing colors as true as it is reasonably possible to obtain in colored reproductions of this type. Colors in the photographs may differ from the color values cited in the detailed botanical description, which accurately describe the actual colors of the new variety 'WP17 PIE54'.

Figure 1:
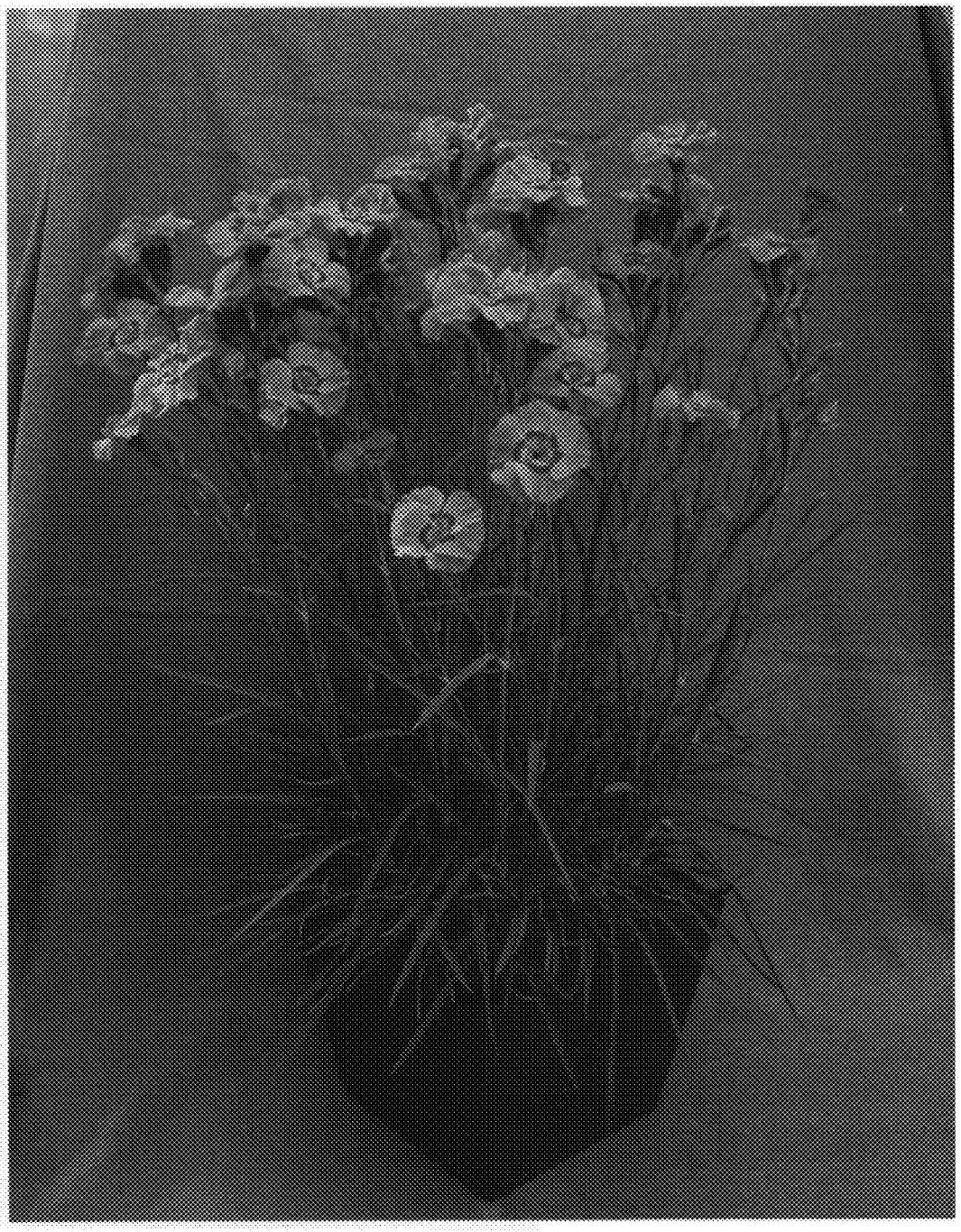
FIG. 1 depicts an entire flowering plant of 'WP17 PIE54'.
Figure 2:
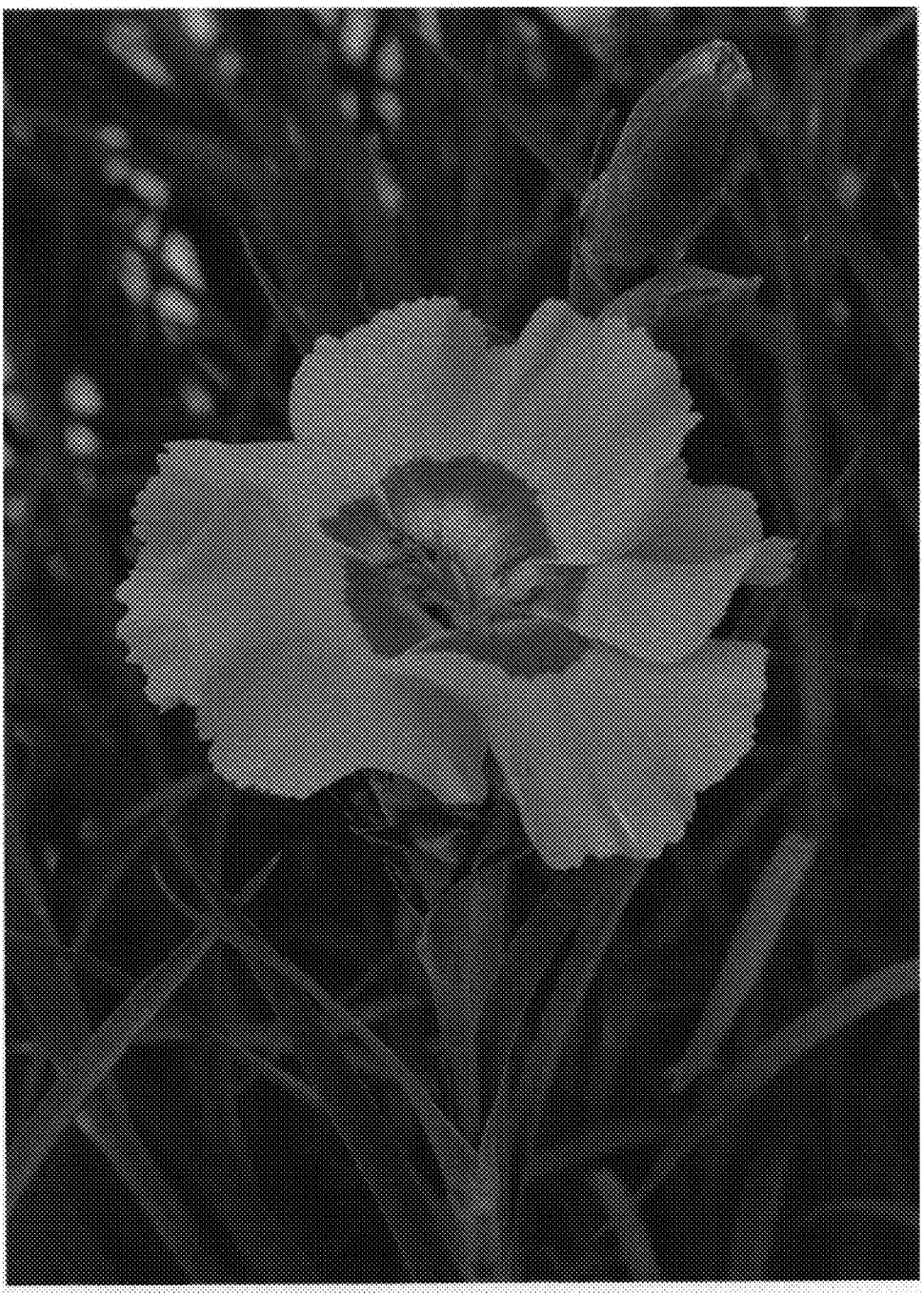
FIG. 2 depicts a close-up view of the flower of 'WP17 PIE54'.

Photographs were taken from a 9 months old plant which was growing in a glasshouse in a 3-liter container at the Inventor's nursery in Dawlish, Devon, United Kingdom. No chemicals were used to treat the plants. All photographs were made using conventional techniques and although colors may appear different from actual colors due to light reflectance they are as accurate as possible by conventional photography.

BOTANICAL DESCRIPTION OF THE PLANT

The following is a detailed description of the new cultivar 'WP17 PIE54'. Data was collected from plants grown in 3-liter containers under an unheated glasshouse in Houndspool, Dawlish, United Kingdom. The color determinations are in accordance with the sixth edition (2015) of The Royal Horticultural Society Colour Chart of The Royal Horticultural Society, London, England, except where general color terms of ordinary dictionary significance are used. No chemicals were used to treat the plants. Growing conditions are typical to other *Dianthus*.

Botanical classification: *Dianthus*.

*Variety*.—'WP17 PIE54'.

*Species*.—*x allwoodii* hort.

*Common names*.—Hybrid *dianthus*, Garden Pink.

*Commercial classification*.—Hardy perennial.

*Use*.—Ornamental plant for pots and containers.

Parentage: 'WP17 PIE54' is a hybrid plant that resulted from the controlled cross-pollination between two *Dianthus* x *allwoodii* plants.

*Female parent plant*.—'Tricia' experimental *Dianthus* plant (unpatented).

*Male parent plant*.—'G152' experimental *Dianthus* plant (unpatented).

Plant description:

*Bloom period*.—May to October.

*Plant habit*.—Compact mounding habit.

*Plant height*.—45 cm in overall height, including flower canopy.

*Plant width*.—30 cm to 35 cm in width.

*Plant hardiness*.—Hardy to minus 15° Centigrade.

*Type*.—Perennial.

*Root system*.—Fibrous.

*Propagation*.—Propagation is accomplished using shoot cuttings.

*Cultural requirements*.—Plant in full sun, well-drained and moderately fertile soil and keep well fertilized and watered.

*Time required to produce a rooted cutting*.—5 weeks are needed to produce a rooted cutting.

*Temperature recommended for cuttings to produce roots*.—The air temperature needed is a minimum of 15° Centigrade air temperature and base heat of 21° Centigrade.

*Crop time*.—6 to 9 months is needed to produce a finished 3-litre container size from a well-rooted cutting.

Stem:

*Shape*.—Cylindrical, solid.

*Dimensions*.—15 cm in length, 4 mm to 6 mm diameter.

*Surface*.—Glabrous and glaucous.

*Color*.—145B, 145C and 145D.

*Branching*.—Numerous shoots from the axils of the lower leaves.

*Internode length*.—4 mm to 8 mm between nodes (before extension of peduncle).

*Node dimensions*.—4 mm in diameter and 5 mm in length.

Leaf:

*Type*.—Evergreen.

*Dimensions*.—10 cm to 12 cm in length, 3 mm in width.

*Color* (*adaxial and abaxial surfaces*).—N189C.

*Shape*.—Linear.

*Division*.—Simple.

*Apex*.—Acute.

*Base*.—Decurrent.

*Venation*.—Absent on the adaxial surface and only one central vein visible on the abaxial surface.

*Margins*.—Entire.

*Attachment*.—Sheathing.

*Arrangement*.—Opposite and spiraling up stem.

*Curvature*.—Weakly recurved.

*Surfaces* (*adaxial and abaxial*).—Strongly glaucous.

*Fragrance*.—Absent.

Inflorescence, flowers:

*Inflorescence*.—Simple cyme.

*Diameter*.—32.0 cm.

*Flower type*.—Single, polypetalous.

*Flower number*.—7 to 9 per stem, borne on lateral stems in 3-4 clusters (typically in pairs, but occasionally single).

*Flower dimensions* (*including calyx*).—31 mm in length and 47 mm in diameter.

*Flower shape*.—Circular.

*Position*.—Flowers are borne far above the foliage.

*Internodes*.—On average, each stem presents 3 internodes between the lowest flower-bearing node and the epicalyx.

*Lastingness*.—10 days at 20° Celsius on the plant; 8 to 10 days off the plant.

*Fragrance*.—Strong, pleasant spicy.

*Flowering period*.—May to October.

Peduncle:

*Shape*.—Cylindrical, solid.

*Dimensions*.—30 cm to 35 cm in length, 2 mm in diameter.

*Surface*.—Glabrous, waxy.

*Strength*.—Strong, rigid.

*Color*.—122A.

Bud:

*Shape*.—Cylindrical.

*Color*.—N138A to N138B on apical half and 144B to 144C on basal half (below the bracts).

*Anthocyanin*.—Absent.

*Dimensions*.—25 mm in length and 7 mm in width.

Petals:

*Corolla*.—Upper and lower part of corolla is flat.

*Petal arrangement*.—Persistent, apopetalous and overlapping.

*Margin*.—Crenate-dentate.

*Indentations*.—3 mm deep, often narrower.

*Texture*.—Soft.

*Type*.—Single.

*Number of petals*.—5.

*Dimensions*.—51 mm in length, 31 mm in width.

*Petal shape*.—Fan shape.

*Petal undulation*.—Moderate.

*Petal surface*.—Glabrous.

*Petal apex*.—Fan shaped, margin crenate-dentate with moderate incisions.

*Petal base*.—Strap shaped, tapering towards base.

*Color pattern*.—Blade is magenta, with a darker magenta band.

*Petal color* (*adaxial surface, freshly opened*).—Ground color of blade: N74A, with small-medium band towards base of petal and appearing as over color 60A. Color of middle of strap: 145C. Color of base of strap: 145D.

*Petal color* (*adaxial surface, fully open and mature*).—Ground color of blade: 67B and N74B, with small-medium band towards base of petal and appearing as over color 61B.

*Petal color* (*abaxial surface*).—Ground color of blade: NN74B; no band or over color present. Color of middle of strap: 145C. Color of base of strap: 145D.

Calyx:

*Dimensions*.—27 mm in length and 8 mm in width.

*Shape*.—Cylindrical.

*Sepals*.—5, fused up to form an eye 7 mm below the apex.

*Sepal dimensions*.—29 mm in length and 5 mm in width.

*Apex*.—Acute.

*Base*.—Truncate.

*Color of sepals, outer surface*.—N138A to N138B on apical half and 144B to 144C on basal half (below the bracts).

*Color of sepals, inner surface*.—139D.

*Anthocyanin*.—Absent.

*Splitting*.—Not observed.

Epicalyx:

*Arrangement*.—Two pairs of bracts, of which one pair (inner epicalyx or bracteoles) is closest to the calyx, and one pair of bracts forms an outer epicalyx.

*Bracts position*.—Both pairs adpressed to each other and to the calyx, and free.

*Bracts shape*.—Deltoid, base short acuminate.

*Bracts dimensions* (*outer epicalyx*).—11 mm in length and 8 mm in width.

*Bracts dimensions* (*inner epicalyx*).—11 mm in length and 11 mm in width.

*Bracts color*.—N138A, N138B, N138C and 144B, 144C, 144D are all present.

*Anthocyanin*.—Absent.

Reproductive organs:

*Stamen number*.—10.

*Stamen dimensions*.—29 mm length and 0.5 mm diameter.

*Color of filaments*.—Whiter than N155A with a purple hue just under the anthers, nearest color is 77D.

*Anther number*.—10.

*Anther dimensions*.—3 mm length and 1 mm in diameter.

*Color of anthers*.—N82B and 90D (when fresh anthers).

*Anther attachment*.—Dorsifixed.

*Pollen*.—Present, 94C, N88C, N87C, N87D, N82C are all present.

*Style number*.—2.

*Style shoulder*.—Absent.

*Color of style*.—Whiter than N155A.

*Style dimensions*.—25 mm to 30 mm in length and 1 mm in width.

*Stigma number*.—One on each style.

*Stigma color*.—N80B.

*Stigma shape and dimensions*.—Linear, 10 mm in length, 2 mm in width.

*Ovary position*.—Superior.

*Ovary dimensions*.—9 mm in length and 5 mm in diameter.

*Ovary shape*.—Obovate.

*Ovary surface and texture*.—Smooth and slightly ribbed.

*Ovary color*.—145A at the uppermost surface, becoming paler 145C to 145D at the lowest surface.

Seed:

*Color*.—202A.

*Length*.—3 mm.

*Diameter*.—2 mm.

*Shape*.—Oval and flattened.

*Surface*.—Crinkled.

*Number*.—Varies, up to 20 per pod.

Diseases and pests: Susceptible to known *Dianthus* pests and disease but no other susceptibilities to pests or disease are known.

COMPARISON WITH PARENTAL LINE AND KNOWN VARIETY

'WP17 PIE54' is distinguishable from the male parent as follows. Whereas the flower color and color combination of 'GI52' is similar to 'WP17 PIE54', the vegetative habit of the two varieties is very different. 'GI52' is much more vigorous than 'WP17 PIE54' and exhibits a looser habit and longer flower stems.

'WP17 PIE54' is distinguishable from the female parent as follows. Whereas the flower stem length and compact habit of 'Tricia' is similar to 'WP17 PIE54', the flower color of the two varieties is different. 'Tricia' has pale pink flowers with a darker eye.

The variety of *Dianthus* which the inventor considers to most closely resemble 'WP17 PIE54' is *Dianthus* Plant Named 'WP15 PIE45' (U.S. Plant patent application Ser. No. 15/731,061). In comparison with 'WP15 PIE045', 'WP17 PIE54' bears more flowers along each flowering stem. Whereas the flowers of 'WP15 PIE45' are predominantly pink-peach in color, the flowers of 'WP17 PIE54' are predominantly magenta in color.

I claim:

1. A new and distinct cultivar of *Dianthus* plant named 'WP17 PIE54' as described and illustrated herein.

* * * * *